United States Patent
Nikolskaja

[11] Patent Number: 5,958,214
[45] Date of Patent: Sep. 28, 1999

[54] ELECTROCHEMICAL SENSOR WITH A SOLID ELECTROLYTE FOR MEASURING THE GAS CONCENTRATION

[75] Inventor: Elena J. Nikolskaja, Sankt Petersburg, Russian Federation

[73] Assignee: MST Micro-Sensor-Technologie GmbH, Hohenschaftlarn, Germany

[21] Appl. No.: 08/544,440

[22] Filed: Nov. 17, 1995

Related U.S. Application Data

[63] Continuation-in-part of application No. 08/232,084, Sep. 12, 1994, Pat. No. 5,538,620.

[51] Int. Cl.$^6$ .................................................. G01N 27/406
[52] U.S. Cl. .................. 205/784; 204/294; 204/402; 204/412; 204/415; 204/421; 204/424; 204/431; 204/432; 205/775; 205/780; 205/783; 205/786.5; 205/787
[58] Field of Search .................................... 204/421–429, 204/431, 432, 415, 294, 402, 412; 205/783, 784

[56] References Cited

U.S. PATENT DOCUMENTS

| | | | |
|---|---|---|---|
| 2,805,191 | 9/1957 | Hersch | 204/431 |
| 3,028,317 | 4/1962 | Wilson et al. | 204/431 |
| 3,811,184 | 5/1974 | Niedrach et al. | 204/421 |
| 4,029,563 | 6/1977 | Binder et al. | 204/432 |
| 5,215,643 | 6/1993 | Kusanagi et al. | 204/431 |
| 5,322,602 | 6/1994 | Razaq | 204/424 |
| 5,358,620 | 10/1994 | Golovin et al. | 204/421 |
| 5,387,329 | 2/1995 | Foos et al. | 204/415 |
| 5,538,620 | 7/1996 | Nikolskaja | 204/421 |
| 5,804,049 | 9/1998 | Chan | 204/418 |

FOREIGN PATENT DOCUMENTS

WO93/10444  5/1993  WIPO.

*Primary Examiner*—T. Tung
*Attorney, Agent, or Firm*—Nikaido, Marmelstein, Murray & Oram LLP

[57] ABSTRACT

The invention relates to an electrochemical sensor to determine the concentration of a gas to be quantified, comprising a housing, a measuring electrode comprising a catalystically active material which causes a reaction of the gas to be quantified, a counterelectrode comprising a carbon material, and a solid electrolyte in contact with the measuring electrode and the counterelectrode, wherein the solid electrolyte is prepared by swelling a solid matrix comprising an acrylate polymer with an electrolytic solution comprising at least one acid, and wherein the carbon material in the counterelectrode has a specific surface of at least 40 $m^2/g$ and comprises reversibly oxidizable or reducible electrochemically active surface compounds.

18 Claims, 2 Drawing Sheets

ELECTROCHEMICAL SENSOR WITH A SOLID ELECTROLYTE FOR MEASURING THE GAS CONCENTRATION

CROSS REFERENCE TO RELATED APPLICATION

This application is a continuation-in-part of U.S. Application Ser. No. 08/232,084, filed Sep. 12, 1994 now U.S. Pat. No. 5,538,620.

BACKGROUND OF THE INVENTION

The present invention concerns an electrochemical sensor for the determination of the concentration of hydrogen, carbon monoxide and silane, fluorine, bromine, iodine, oxygen, sulfur dioxide, methane, ethane, ethylene, acetylene and other gases. This sensor can inter alia be used for manufacturing portable, self-powered and easily operated instruments to measure and monitor the gas concentration.

Gas analyzers for continuously monitoring the surrounding medium are widely used in many fields such as in the automatic control of technological processes, explosion protection, ecological monitoring etc.. The construction of such analyzers may be based on electrochemical sensors. Various types of sensors are known for measuring and monitoring the gas concentration.

A known type of sensor (N. I. Globa: "Razrabotka i issledovanie electrochimicheskich datchikov konzentratsii kisloroda i vodoroda", author's dissertation paper Leningrad Institute of Technology, 1985, p. 11–14) contains a measuring electrode and a counterelectrode which are located in a liquid electrolyte. The measuring electrode is completely or partially composed of a catalytically active material. The counterelectrode is manufactured from an electrochemically active material, the selection of this material being dependent on the gas to be determined. If the material has low electrical conductivity, the counterelectrode is manufactured from a mixture of this material and carbon, in which case the carbon increases the electrical conductivity. The counterelectrode in an oxygen sensor is for example made of lead and in a hydrogen sensor it is made of a mixture of manganese dioxide and carbon.

When a gas the concentration of which is to be determined, is fed to the sensor an electrochemical oxidation (in the case of lead) or reduction (in the case of manganese dioxide) of the electrochemically active counterelectrode material takes place. This system which is composed of 2 electrodes generates an electrical current in an outer conductive circuit the magnitude of which is proportional to the gas concentration. This current can be utilized as a measure for the gas concentration.

The active material (lead or manganese dioxide) is consumed in the chemical reactions on the counterelectrode which limits the life of the sensor.

Passivation of the surface of the counterelectrode by products of the chemical reactions that take place on the electrode and diffusion of reaction products towards the measuring electrode can lead to errors in the measured signals which consequently decreases the reliability of the sensor. In order to reduce these effects, sensors which operate according to the principle stated above must be made with relatively large dimensions and large amounts of material.

A further known sensor for measuring the gas concentration (JP-A-59-28358) contains a measuring electrode made of a catalytically active material, an electrolyte and a counterelectrode which is composed of a mixture of carbon and an electrochemically active organic substance such as chloroquinone or monomeric and polymeric iron and cobalt phthalocyanine. The electrochemically active substance acts as a catalyst in the electrochemical reduction of oxygen.

When the gas to be measured is fed to the sensor it is oxidized on the measuring electrode. Accordingly a reduction of atmospheric oxygen or of specially supplied oxygen takes place on the counterelectrode which is made possible by the active components (catalysts). The catalysts are alternately oxidized and reduced during sensor operation. However, these two reactions are not absolutely reversible which leads to consumption of the catalysts and limits the life of the sensor. Moreover sensor reliability is only poor since the surface of the counterelectrode may be passivated by the products of oxygen reduction and these reaction products may diffuse towards the measuring electrode. A further disadvantage of the sensor is that the liquid electrolyte may dry out. However, the use of a solid electrolyte in such a sensor is also very difficult due to the need to generate a four-phase boundary "carbon-catalyst-electrolyte-oxygen".

Another restriction of using sensors of the above kind is that they can only operate for longer periods while being fed with oxygen i.e. in oxygen-containing media or with a specially implemented oxygen feed. Furthermore the use of liquid electrolytes results in a low mechanical strength of the sensor.

A sensor developed earlier by the same inventor contains a measuring electrode made of a catalytically active material, an electrolyte and a counterelectrode made of chemically pure carbon having a specific surface of 1,000 to 1,700 $m^2/g$. When the sensor is contacted with a gas the concentration of which is to be measured, the gas is electrochemically ionized at the measuring electrode. A charging process of the electrical double layer at the carbon-electrolyte boundary takes place at the counterelectrode. The resulting current measured in an external conductive circuit is proportional to the gas concentration and is used as a measure of the concentration.

Since the counterelectrode does not itself contain any electrochemically active components the life of the sensor is determined by the charging time of the electric double layer. An adequately long life can only be achieved when using a chemically pure carbon with a high specific surface (larger than 1,000 $m^2/g$). However, in this case the life of such a sensor with a size suitable for portable instruments is also only about 2 years.

Furthermore the manufacture of chemically pure carbon for the counterelectrode is difficult because oxygenous compounds are formed at the surface during the synthesis and activation of carbon. Due to the high adsorptivity of carbon it is practically impossible to prevent interactions between the electrolyte components and the chemically pure carbon. In turn such interactions can lead to a change of the potential of the counterelectrode and falsify the signals.

SUMMARY OF THE INVENTION

The object of the invention is to develop an electrochemical sensor for measuring the gas concentration which is distinguished by its high reliability and life. This object is achieved according to the invention by the sensor which is described in the following. Further objects can be deduced from the following description.

One subject matter of the invention is an electrochemical sensor for measuring the concentration of a gas which comprises a housing (1), a measuring electrode (5) containing a catalytically active material which is capable of ionizing the gas to be determined, a counterelectrode (3) which contains a carbon material and an electrolyte which is in contact with the measuring electrode and counterelectrode and is embedded in a solid matrix, the carbon material in the counterelectrode having a specific surface of at least 40 $m^2/g$ and containing electrochemically active surface compounds that can be reversibly oxidized or reduced which is characterized in that the electrolyte is prepared by soaking a polymer in a solution of an acid or a mixture of acids.

The catalytically active material of the measuring electrode is a material which on the one hand must be resistant to the electrolyte and on the other hand catalyzes the reaction of the gas to be measured. For a number of sensors platinum can for example be used as the catalytically active material. The catalytically active material in a fluorine sensor can additionally be made of carbon and in an oxygen sensor it can be made of gold. The measuring electrode can be completely or partially composed of the catalytically active material i.e. it is for example possible to use a platinum wire or a platinum mesh or even an electrode which is merely coated with platinum.

The counterelectrode of the sensor according to the invention contains a carbon material i.e. it is completely or partially composed of the above stated carbon material. As a rule the electrochemically active compounds on the surface of the counterelectrode are compounds that are formed on the surface of the carbon material during its production process. Such compounds can be reversibly oxidized and reduced. These are for example compounds of the hydroquinone/quinone type. A review of electrochemically active surface compounds is given for example in M. P. Tarasevitch, Electrochimija uglerodnych materialov (electrochemistry of carbon materials), Nauka, Moscow, 1984.

When current flows through the counterelectrode of the sensor according to the invention, the electric double layer at the electrode-electrolyte boundary becomes charged thus leading to a reversible reduction or oxidation of the electrochemically active compounds on the surface of the counterelectrode. The carbon material in the counterelectrode is preferably an activated carbon with electrochemically active surface compounds. Due to the high specific surface and the chemical properties of activated carbon, the capacitance of the counterelectrode and the number of electrochemically active surface compounds is very high. As a result when the sensor is operated the potential of the counterelectrode only changes very slowly and therefore remains for a long time in the range of the electrochemical stability of the electrolyte.

When gas is supplied a reaction of the gas to be determined takes place at the measuring electrode. The double layer of the counterelectrode becomes charged and the surface compounds are reversibly oxidized and reduced. If the electrodes are connected by electrical contacts to an external conductive circuit, the current flowing in the external conductive circuit can serve as a measure of the gas concentration.

DETAILED DESCRIPTION OF THE INVENTION

Figure 1:
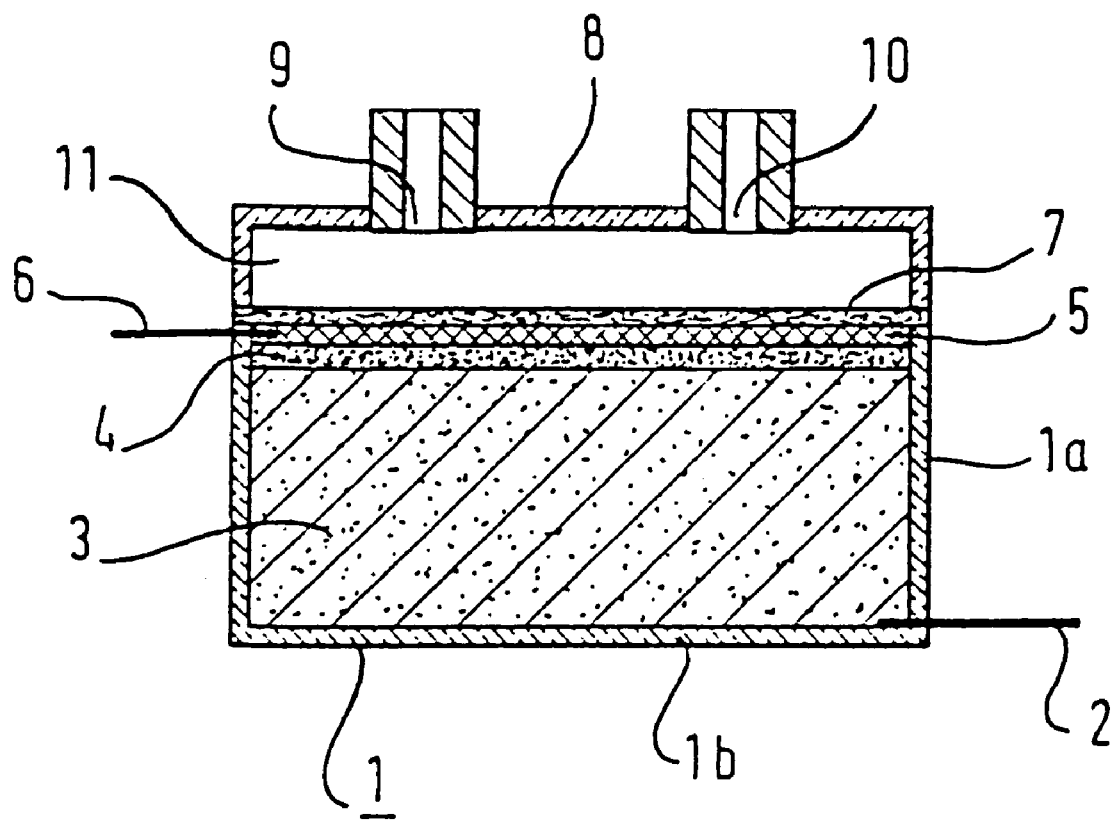
FIG. 1 shows a schematically simplified vertical section through a first embodiment of a sensor according to the invention.

The life of the sensor according to the invention depends on the capacitance of the double layer and on the number of the electrochemically active surface compounds. The larger the specific surface of the counterelectrode the longer is the life of the sensor.

The electrochemical properties of the active surface compounds of the activated carbon used preclude electrode passivation or diffusion of the reaction products towards the measuring electrode. This leads to a high reliability of the sensor.

The presence of oxygen at the counterelectrode is not required in the sensor according to the invention which in turn enables applications in oxygen-free media and improves the reliability and mechanical stability of the sensor.

The life of the sensor is greatly increased without having to increase its size and weight by the presence of chemical surface compounds in the carbon material of the counterelectrode which can be reversibly oxidized and reduced. Therefore the sensor according to the invention can be designed as a portable, self-powered instrument.

Since as a rule there are no chemical interactions with the electrolyte in the case of a carbon material containing chemical surface compounds it is possible to preclude unanticipated changes in the counterelectrode potential which again increases the reliability of the sensor.

The use of activated carbon with a low specific surface (e.g.: 40 $m^2/g$) and electrochemically active surface compounds already enables the manufacture of sensors with adequate properties. The use of activated carbon with a high specific surface (1,000–3,000 $m^2/g$) enables sensors to be manufactured with a very long life without the need to enlarge the sensors.

It is advantageous in a sensor according to the invention when the counterelectrode is located in a hermetically sealed chamber. In this way the counterelectrode is protected from contact with impurities and consequently the life of the sensor is increased.

The electrolyte is present embedded in a solid matrix. This makes it impossible for the electrolyte to dry out and as a result the life of the sensor is increased. Moreover the mechanical stability of the sensor is increased. The electrolyte is embedded in a solid matrix by manufacturing the electrolyte by soaking a polymer in a solution of an acid or a mixture of acids.

The polymer preferably contains a polymer based on acrylate e.g. a polyacrylate or a polymethacrylate, the polymer particularly preferably contains polymethacrylate. Furthermore the polymer can also contain a polyolefin polymer e.g. a polyethylene. Mixtures of polymers based on acrylate and polyolefins are particularly preferred in a weight ratio of 10:1 to 1:10, in particular of 5:10–1:5.

For the production of the solid electrolyte, the polymer is heated if desired together with the carbon material pressed under increased pressure and then impregnated with an acid or a mixture of acids. The impregnation process can cause the solid electrolyte to swell or expand particularly when using a polymer based on acrylate. This swelling or expansion process leads to particularly preferred solid electrolytes. The duration of the swelling process is several hours and preferably ca. 10 to 100 hours.

In addition it is possible to use a solid electrolyte in a separator.

In some cases in particular when the diffusion limiting current has a narrow range, it may be advantageous to use a sensor with three electrodes. Such a sensor additionally contains a reference electrode apart from the measuring electrode and the counterelectrode. This reference electrode serves to keep the measuring electrode at an essentially constant potential (namely in the range of diffusion limiting current). The reference electrode can be manufactured from a catalytically active material e.g. from the same material as the measuring electrode. In addition the reference electrode should have a large surface in order to prevent polarization. The reference electrode is inserted in the electrolyte e.g. between the measuring electrode and the counterelectrode. When such a three-electrode sensor is used, the same processes take place on the measuring and counterelectrodes as with a sensor having only two electrodes.

In a further preferred embodiment of the invention the sensor can additionally contain one or several supplementary electrodes. The use of such a supplementary electrode enables the sensor to regenerate during its operation by discharge of the counterelectrode. In this case such a voltage is set between the counterelectrode and the supplementary electrode that processes proceed in the counterelectrode which counteract the charging of the counterelectrode during normal sensor operation. The manner of operation of a sensor with the supplementary electrode is described in connection with the elucidation of FIG. 2.

In yet another preferred embodiment of the invention the sensor may also contain several measuring electrodes e.g. two measuring electrodes. Such a sensor is constructed similarly to a sensor with a supplementary electrode except that a second measuring electrode is used with a diffusion membrane instead of the supplementary electrode. A voltage is applied between this measuring electrode and the counterelectrode which is required for measuring the concentration of the gas to be measured. The second measuring electrode is based on the same principle as the first measuring electrode. The selection of the catalytically active material and the voltage determines which reaction takes place at the second measuring electrode i.e. in particular which gas is reacted.

In this embodiment it is advantageous when a gas to be measured is oxidized at one of the measuring electrodes and a second gas is reduced at the second electrode. In this case the counterelectrode is charged during operation of the first measuring electrode and the counterelectrode is simultaneously discharged during operation of the second measuring electrode. This results in a significant increase of the life of the electrochemical sensor since the counterelectrode is no longer charged during alternating and/or simultaneous operation of the measuring electrodes. Thus the second measuring electrode serves to concurrently measure a second gas concentration and as a supplementary electrode to discharge the counterelectrode.

In addition the present invention concerns a method for determining the concentration of one or several gases using an electrochemical sensor according to the invention. The method according to the invention allows the determination of arbitrary gases provided that they can be reacted at the catalytically active measuring electrode. Examples of suitable gases are hydrogen, fluorine, chlorine, bromine, iodine, oxygen, sulfur dioxide, silane, carbon monoxide, nitrogen dioxide, methane, ethane, ethylene and acetylene. Preferred gases are hydrogen, silane, carbon monoxide or oxygen.

When two measuring electrodes are used, two different gases (for example hydrogen and oxygen) can be determined simultaneously.

In a preferred embodiment the method according to the invention is carried out by connecting the electrochemical sensor via terminals to an external conductive circuit, setting a suitable external potential such as 0.1 to 0.6 volts between the electrodes of the sensor and measuring the current in the external conductive circuit which is proportional to the concentration of the gas to be measured. When determining hydrogen a sensor is for example used which contains a measuring electrode made of platinum, a counterelectrode made of activated carbon having a specific surface of 1,000–1,700 $m^2/g$ and an electrolyte based on a strong mineral acid (e.g. $H_2SO_4$, $H_3PO_4$ etc.), an external potential of about 0.3 volts being set between the electrodes. The electrolyte can be embedded in a solid matrix.

A further advantage of the gas determination with the aid of a sensor according to the invention is that the sensor can be regenerated after a predetermined operating period by reversing the electrode polarization by applying an external voltage.

In addition the invention concerns a solid electrolyte which is particularly suitable for use in an electrochemical sensor especially in a sensor according to the invention. This solid electrolyte is composed of a polymer in which an electrolyte solution is incorporated. For its production a suitable polymer is impregnated with a liquid electrolyte such as an aqueous or aqueous/organic solution of acids, salts or bases. Within the scope of the sensor according to the invention a solid electrolyte is produced by impregnating a polymer which contains a polymer based on acrylate and in particular polymethylmethacrylate with an acid or a mixture of acids. Suitable acids are for example sulfuric acid, trifluoro-methanesulfonic acid and phosphoric acid or a mixture thereof.

A further object is a process for the production of a solid electrolyte which is composed of a polymer in which an electrolyte solution is incorporated which is characterized in that the electrolyte is produced by soaking a polymer in a solution of an acid or a mixture of acids and the use of a solid electrolyte produced by a process according to the invention in an electrochemical sensor.

Some preferred embodiments of the sensor according to the invention are described in the following. The attached FIG. 1 shows a schematically simplified vertical section through a first embodiment of a sensor according to the invention. As shown in FIG. 1 the sensor comprises a housing 1 made of an inert dielectric material such as Teflon or plexiglass.

The housing may have dimensions of for example 20 mm in diameter and 40 mm in height. Two apertures for electrode contacts (2,6) are located in the cylindrical sidewall 1a of the housing. The contact wire 2 which acts as a contact for the counterelectrode in the finished sensor is placed at the bottom 1b of the housing and is passed through one of the apertures. The counterelectrode 3 which is prepared from active carbon with electrochemically active surface compounds is inserted into the housing. The specific surface of the counterelectrode is 1,000 $m^2/g$ to 1,700 $m^2/g$ i.e. its porosity is very high. The counterelectrode is impregnated with the liquid electrolyte. The electrolyte which is composed of a mixture of polymerizable monomers such as methylmethacrylate and a polymerization initiator such as for example azo-bis(iso-butyronitrile) and an ionically conductive substance (e.g. an acid in the case of a $H_2$ sensor) is poured into the housing and allowed to stand for about 30 minutes. During this period the liquid can penetrate into the pores of the counterelectrode. Afterwards the counterelectrode is compressed by a plunger and the housing with the counterelectrode is placed in a heating apparatus. Incomplete prepolymerization takes place in the heating apparatus at a particular appropriate temperature (e.g. 120° C.) within a suitable time interval (e.g. 2 hours) which results in an increased viscosity of the electrolyte. The extent of this polymerization can be controlled by the external factors (time, temperature, if desired pressure), by the initiator concentration and if desired by addition of a polymerization inhibitor. A "block" which consists of the counterelectrode, the electrolyte and the contact wire is formed in the housing by the prepolymerization. Subsequently the housing with the counterelectrode block is removed from the heating apparatus and a separator 4 is laid on the block. The separator has the shape of a round disk with a thickness of about 50 μm and a diameter which corresponds to the diameter of the housing. The separator is preferably manufactured from a porous polymer material which is resistant to the electrolyte used e.g. from polypropylene.

Subsequently the measuring electrode 5 made of a catalytically active material is placed on the separator. The measuring electrode can for example be manufactured in the form of a platinum mesh of about 50 μm thickness and with a diameter that corresponds to the diameter of the separator. The contact wire 6 which is connected to the measuring electrode is passed through one of the apertures in the housing. The separator and the measuring electrode are pressure-joined to the counterelectrode whereby the separator becomes impregnated with the electrolyte and the measuring electrode is moistened. The sensor prepared in this manner is again placed in a heating apparatus where the electrolyte is completely polymerized under suitable conditions (e.g. within one hour at a temperature of 110° C.).

Afterwards a gas-permeable diffusion membrane 7 which preferably consists of a polymer e.g. Teflon is placed on the measuring electrode. The membrane should lie closely on the electrode. A cap 8 which is placed on the housing presses the membrane against the measuring electrode. This cap can for example be made of the same material as the housing. The cap comprises intake apertures (9, 10) through which the gas can reach the sensor. If necessary the cap can also have fastenings for lines through which a gas flow can be fed into or evacuated from the sensor.

A gas chamber 11 is present between the cap 8 and the diffusion membrane 7. The cap, the membrane and the housing are permanently joined together e.g. glued together. In this way the counterelectrode is located in a sealed chamber enclosed by the housing and the separator. The contact wires are connected to an external conductive circuit (not shown in the figure) which contains an ammeter and a voltage source.

A further possible embodiment of the sensor contains a liquid electrolyte instead of a solid electrolyte. In this case the counterelectrode is impregnated with the electrolyte and then a rigid porous membrane which is for example composed of the same material as the housing is inserted in the housing. A separator and the measuring electrode are then placed on this membrane as in the sensor described above. Polymerization in the heating apparatus is not carried out. Otherwise the sensor is manufactured in the same manner as the sensor with the solid electrolyte.

When the sensor is in operation a gas mixture containing a gas to be determined passes through the apertures 9, 10 into the gas cell 11 and diffuses through the diffusion membrane 7 to the measuring electrode 5. The membrane ensures steady gas-mixture feed to the measuring electrode. The potential of the measuring electrode can be selected in such a way that only the gas to be determined is reacted. The external voltage source to which the contact wires are connected supplies the required potential difference relative to the counterelectrode 3.

Since the potential of the counterelectrode only changes very slowly due to its high capacitance and the potential difference is kept constant, the potential of the measuring electrode also only changes very slowly. The potential of the measuring electrode is in the limiting current range of the gas reaction. Gas that reaches the measuring electrode is reacted and the ions that form in the electrolyte during the reaction migrate to the surface of the counterelectrode. As a result a current flows in the external conductive circuit. The separator precludes electrical contact between the two electrodes while allowing ions through. As a result of the charge migration to the counterelectrode the electric double layer at the boundary between the electrolyte and the counterelectrode charges up. The ions are adsorbed on the surface of the counterelectrode.

The processes that take place in the electric double layer are described in detail in the book by B. B. Damaskin, O. A. Petry "Vvedenie v elecktrochimicheskuju kinetiku", 1975, Moscow High School, p. 105–130.

The counterelectrode potential changes as the double layer is being charged. Upon reaching corresponding potential values, reversible oxidation or reduction of the chemical surface compounds take place on the counterelectrode surface. These processes are described in the book by M. R. Tarasevitsch "Elektrochimia uglerodnych materialov", 1984, p 253, "Nauka", Moscow.

The current in the external conductive circuit is proportional to the concentration of the gas which is being reacted at the measuring electrode with formation of ions. When a current flows, the charge of the electric double layer increases with time and the potential of counterelectrode changes.

The electrochemical stability of the electrolyte used determines the allowable change in potential. When the counterelectrode potential exceeds the potential for electrolyte decomposition, the current in the external conductive circuit will no longer be proportional to the gas concentration. This leads to errors in the determination of the gas concentration i.e. it is possible to determine the gas concentration as long as the counterelectrode potential is in the permissible range. The life of the sensor corresponds to the period in which the change in the counterelectrode potential does not exceed the maximum allowable change.

The life of the sensor is calculated in the following. The capacitance of the double layer C corresponds to charge $q_c$ which has to be supplied to the counterelectrode in order to change its potential by one unit:

$$C = \frac{q_c}{\psi} \quad (1)$$

If only the double layer is charged on the counterelectrode, the charge supplied by the current I during the period $t_c$ would change the potential of the counterelectrode by $\Delta\psi$:

$$c = \frac{I \cdot t_c}{\Delta\psi} \qquad (2)$$

If $\Delta\psi$ corresponds to the maximum allowable change in potential and if only the double layer is charged, the life of the sensor is then given by:

$$t_c = \frac{c \cdot \Delta\psi}{I} \qquad (3)$$

The double-layer capacitance is proportional to the size S of the counterelectrode ($C=K_c \times S$, $K_c$ being a constant of proportionality) and it follows from formula 3 that:

$$t_c = \frac{K_c \cdot S \cdot \Delta\psi}{I} \qquad (4)$$

In addition reversible reduction or oxidation processes of chemical surface compounds take place on the counterelectrode. These processes (Faraday processes) are described by Faraday's laws:

$$q_f \times K_f = \Delta m \qquad (5)$$

In which $\Delta m$—is the reacted quantity of material $K_f$—is the proportionality constant $q_f$—is the quantity of charge which is consumed for reduction or oxidation The quantity of charge $q_f$ results from the current I and the period in which the Faraday processes take place: $q_f = I \times t_f$. This results in:

$$I \times t_f \times K_f = \Delta m \qquad (6)$$

Various surface compounds are present on the counterelectrode which have different values of potential for reduction or oxidation. These values are within the permissible range of potential $\Delta\psi$. The Faraday capacitance (capacitance of the electrode which is linked to the sequence of the Faraday processes) is an order of magnitude higher than the double layer capacitance. Therefore the change in the counterelectrode potential is much slower when the surface compound is reduced or oxidized than when only one double layer is charged. The potential remains practically unchanged for some time in many regions of the charging curve (the dependency of potential on the quantity of charge supplied). As a result of the Faraday processes the counterelectrode potential remains much longer in the permissible range thus greatly increasing the life of the sensor.

After a specific surface compound has been completely reduced or oxidized, the potential again begins to change according to equation (2) until a value is reached at which another surface compound is reduced or oxidized.

Thus the potential of the counterelectrode varies according to equation (2) with interruptions caused by Faraday processes.

The following applies to a surface compound i:

$$I \times t_{fi} \times K_{fi} = \Delta m_i \qquad (7)$$

in which:

$t_{fi}$—is the period for reduction or oxidation of the surface compound i $K_{fi}$—is the proportionality constant for the surface compound i $\Delta m_i$—is the reacted quantity of the surface compound i The total period during which the Faraday processes take place is given by:

$$\sum_i t_{fi} = \sum_i \frac{\Delta m_i}{I \cdot K_{fi}} = \frac{1}{I} \sum_i \frac{\Delta m_i}{K_{fi}} \qquad (8)$$

The quantity of surface compounds is proportional to the surface S of the counterelectrode:

$$\Delta m_i = K_i \times S \qquad (9)$$

It follows that:

$$\sum_i t_{fi} = \frac{1}{I} \sum_i \frac{K_i \cdot S}{K_{fi}} = \frac{S}{I} \sum_i \frac{K_i}{K_{fi}} \qquad (10)$$

The life t of the sensor corresponds to the sum:

$$t = t_c + t_{fi} \qquad (11)$$

It follows that:

$$t = \frac{K_c \cdot S \cdot \Delta\psi}{I} + \frac{S}{I} \sum_i \frac{K_i}{K_{fi}} = \frac{S}{I}\left(K_c \cdot \Delta\psi + \sum_i \frac{K_i}{K_{fi}}\right) \qquad (12)$$

The life of the sensor is the longer the larger the surface of the counterelectrode, the larger the permissible change in potential, the greater the quantity of surface compounds and the smaller the current is that flows through the electrode.

The current magnitude can be adjusted by selection of the materials, by the construction and the position of the membrane 7 and of the measuring electrode 5. These parameters must be selected in such a way as to ensure the required measurement accuracy and the appropriate measuring range. As a rule the current is in the range of $\mu A$.

The permissible change in the counterelectrode potential depends on the electrochemical stability of the electrolyte. This change is 0.4 to 0.6 volts for the solid electrolytes used.

With a specific surface of the activated carbon of 1,000–1,700 $m^2/g$ and a counterelectrode of about 10 g the surface of the counterelectrode will be very large reaching several thousand square meters. Such a surface results in very high double-layer capacitance (several thousand farads [F]); for example the specific capacitance for activated carbon with a specific surface of 1,500 $m^2/g$ is 400 F/g.

For a counterelectrode made of 10 g activated carbon, a permissible change in potential of 0.4 V and a current of 20 $\mu A$, equation 3 results in:

$$t_c = \frac{400 \times 10 \times 0.4}{20 \cdot 10^{-6}} = 80 \times 10^6 \text{ s} \approx 20{,}000 \text{ h}$$

The quantity of chemical surface compounds may be estimated. According to M. R. Tarasevitsch ("Elektrochimia uglerodnych materialov", 1984, Nauka, Moscow, p. 35) the maximum oxygen content in activated carbon is 0.5 to 3 mmol/g. Oxygen is present on the surface of the activated carbon inter alia in the form of compounds such as quinone-hydroquinone which has been demonstrated by the empirically determined reversibility of electrochemical processes on the surface of activated carbon in the potential range used and this is known from the literature (catalogue, NEC, Japan, 1982). Assuming that about half the quantity of oxygen is contained in such compounds, the amount of these compounds may be calculated as a maximum of about 3 mmol/g of activated carbon (the functional group of quinones contains one oxygen atom). Since the reduction or oxidation of the functional group of compounds of the quinone-hydroquinone type is linked to the transfer of one electron, the quantity of charge required for the reduction or oxidation of such compounds is given by $$q_f = 26.8A \times h \text{ mol}^{-1} \times 3 \times 10^{-3} \text{ mol/g} = 0.08A \times h/g$$

$$q_f = t_f \times I \text{ results in}$$

$$t_f = \frac{q_f}{I} \tag{13}$$

thus for the above example (the electrode having a weight of 10 g)

$$t_f = \frac{0.08 \cdot 10}{20 \cdot 10^{-6}} = 40,000 \text{ h}$$

According to equation (11) it follows that:

$$t = t_c + t_f = 20,000 + 40,000 = 60,000 \text{ h}$$

i.e. more than 6 years.

If the specific surface of the carbon is 2,000 $m^2/g$ a life of about 80,000 h, i.e. about 9 years, results from such an estimation.

The life of the sensor is increased by using activated carbon with a higher specific surface but entails higher costs. The maximum known specific surface of activated carbon is about 3,000 $m^2/g$ (G. Elwin, S. Stail "Nositeli i naniesiennyie katalisatory. Teoria i praktika", 1991, Chimia, Moscow, p. 111).

The use of activated carbon with a specific surface of 40 to 1,000 $m^2/g$ results in sensors with a life which corresponds to that of most known sensors (about 1 year). for example a counterelectrode made of activated carbon with a specific surface of 40$m^2/g$ and a weight of 50 g has for example a life of about 8,000 hours (just under 1 year).

The electrochemical properties of the chemical surface compounds preclude passivation of the counterelectrode and also diffusion of reaction products to the measuring electrode which ensures sensor reliability. The electrochemical reactions in which the chemical surface compounds participate are reversible.

A known system, the so-called super-capacitor (catalogue of the Nippon Electric Company, Japan 1982) contains two electrodes made of activated carbon and is used as a capacitor with a very high capacitance. In this system the same processes take place at both electrodes as described above for the counterelectrode. Due to the reversibility of the electrochemical processes at the activated carbon electrodes and the consequently unlimited number of charge-discharge cycles, capacitor life is unlimited. 15,000 cycles were achieved without change in the parameter.

According to data from the literature and from experiments, the sensors according to the invention can be regenerated after their life expires by reversing the electrode polarization while applying an external voltage. Then reactions take place on both electrodes of the sensor which are the reverse of the electrochemical reactions described above.

In a hydrogen sensor hydrogen is for example produced at the measuring electrode from the protons of the electrolyte ($2H^+ + 2e^- \rightarrow H_2$) when the polarization is reversed. At the counterelectrode the electrochemical double layer discharges and the chemical surface compounds that are reduced during sensor use are oxidized or the oxidized chemical surface compounds are reduced. When the quantity of charge which flows in the reverse direction corresponds to the quantity of charge that drained away during operation of the sensor, the counterelectrode is again in its initial state with regard to charge and potential. During the charging process an amount of hydrogen is generated at the measuring electrode which corresponds to the amount of hydrogen that was reacted during operation.

The sensor returns to its initial state and can again be used to determine hydrogen concentrations.

Since the processes on the measuring electrode in a hydrogen sensor are reversible, the number of "operation-regeneration" cycles is theoretically unlimited i.e. the theoretical life of the sensor is also unlimited provided it is always regenerated. Since the counterelectrode withstands at least 15,000 "operation-regeneration" cycles, the ability to regenerate the sensor is determined by the measuring electrode. The number of cycles for an oxygen sensor is for example about 50.

The possibility to regenerate the sensor increases its life considerably compared to all known electrochemical gas sensors. Thus it is advantageous in the sensor according to the invention when the electrolyte contains those ion species that are also formed in the gas reaction at the measuring electrode. When such an electrolyte is used the composition and the concentration of the electrolyte remains virtually constant. For example an electrolyte containing protons is used in the hydrogen sensor ($H_2 \rightarrow 2H^+ + 2e^-$), an electrolyte containing fluorine ions is used in the fluorine sensor ($F_2 + 2e^- \rightarrow 2F^-$), an electrolyte containing chlorine ions is used in the chlorine sensor ($Cl_2 + 2e^- \rightarrow 2Cl^-$).

However, other electrolytes can also be used, for example an electrolyte containing $F^-$ ions can be used to determine the chlorine concentration. However, this leads to a change in the electrolyte composition during the gas reaction and may result in a shortening the of the sensor life and falsification of the signals due to a change in the equilibrium potential of the measuring electrode.

Figure 2:
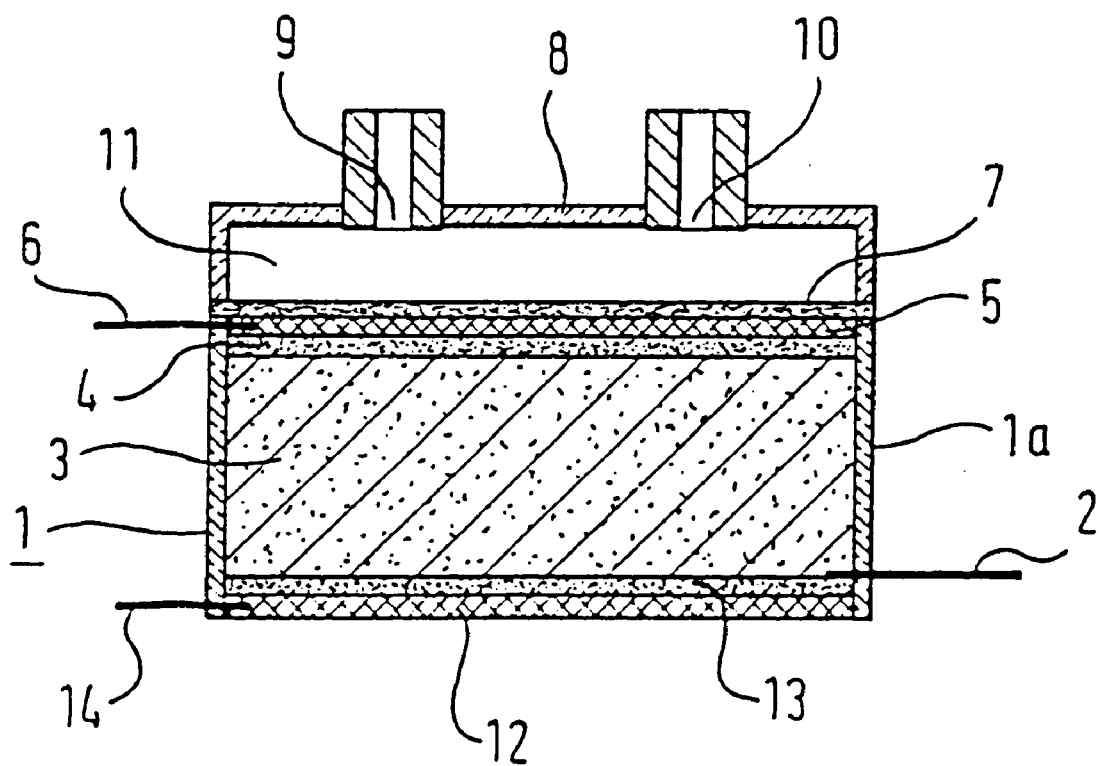
FIG. 2 shows a schematically simplified vertical section through a second embodiment of a sensor according to the invention, which contains a supplementary electrode apart from the measuring electrode and the counterelectrode.

FIG. 2 shows a second embodiment of the sensor according to the invention which contains a supplementary electrode apart from the measuring electrode and the counterelectrode. In this case the sensor can be regenerated while in operation. The reference numbers in FIG. 2 correspond to those in FIG. 1.

The housing of the sensor in FIG. 2 has no backwall (1b in FIG. 1). The sensor instead contains a supplementary electrode 12 which is separated by a separator 13 from the counterelectrode. The supplementary electrode can be manufactured from a catalytically active material (e.g. platinum mesh). The contact wire 14 acts as a contact for the supplementary electrode. A voltage is applied between the counterelectrode and the supplementary electrode during operation of the sensor. The gas concentration is measured as described for a sensor without supplementary electrode. The supplementary electrode allows regeneration of the sensor during its operation. For this purpose the voltage between the supplementary electrode and the counterelectrode is selected in such a way that processes proceed in the supplementary electrode which are the reverse of those occurring during normal sensor operation (in relation to the measuring electrode). If for example the counterelectrode acts as cathode in relation to the measuring electrode so that during sensor operation the electric double layer is charged and the surface compounds are reduced, the counterelectrode acts as anode in relation to the supplementary electrode so that there is a concurrent discharge of the electric double layer and oxidation of the surface compounds on the counterelectrode. In this process an electrochemical reaction takes place on the supplementary electrode e.g. a reduction of atmospheric oxygen or hydrogen generation from the electrolytes. The rate of these processes depends on the voltage between supplementary electrode and counterelectrode. In this case the voltage is advantageously selected in such a way that the current flowing between these electrodes in the external conductive circuit has the same value (but the opposite direction) as the average current that flows between the measuring electrode and the counterelectrode.

In this manner a simultaneous charging and discharging of the counterelectrode takes place during sensor operation. This results in a very substantial increase in the life of the sensor. This life is determined by the permissible change in the counterelectrode potential. The counterelectrode potential changes much more slowly when the supplementary electrode is used. The life of such a sensor having a supplementary electrode is limited by the possible change in electrolyte composition during the electrochemical reactions that take place at the measuring and supplementary electrodes. However, in many cases the life of such a sensor is theoretically unlimited e.g. if hydrogen is generated on the supplementary electrode in a hydrogen sensor, the composition of the electrolyte is not changed. The following reactions occur in such a sensor:

at the measuring electrode:

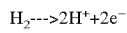

$H_2 \longrightarrow 2H^+ + 2e^-$ at the supplementary electrode:

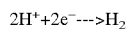

$2H^+ + 2e^- \longrightarrow H_2$

Introducing of the supplementary electrode can increase the life of the sensor can be increased or/and decrease the dimensions of the sensor (the amount of activated carbon) without having an adverse effect on the life of the sensor.

The invention is further elucidated by the following examples.

EXAMPLE 1

A hydrogen sensor according to the invention was manufactured and tested. The sensor housing was made of polyethylene. The counterelectrode was prepared from an activated carbon fabric with a thickness of 30 $\mu$m and a specific surface of 1,500 m$^2$/g. The counterelectrode had a diameter of 20 mm. The total weight of the electrode was 2.3 g. The measuring electrode was manufactured from a platinum mesh and had a diameter of 19 mm. The separator was prepared from polypropylene. A liquid electrolyte (38% sulphuric acid) was used. A polyethylene foil with a thickness of 20 $\mu$m was used as a diffusion membrane. The sensor had an inside diameter of 24 mm, a height of 20 mm and a weight of 3 g. A micro-ammeter and a voltage source were included in the external conductive circuit. The permissible change in the counterelectrode potential in the electrolyte was 0.4 volts.

A gas mixture of hydrogen and nitrogen was used for gassing.

The hydrogen concentration was known and was up to 48%. At a H$_2$ concentration of 4% and a polarization voltage of +0.3 V (measuring electrode relative to the counterelectrode) the current was 10 $\mu$A. With a specific surface of activated carbon of 1,500 m$^2$/g, the specific capacitance was about 400 F/g and which enabled the life t to be estimated from equations 3, 11, 13:

$$t = \frac{400 \times 2.3}{10 \times 10^{-6} \times 3,600} + \frac{0.08 \times 2.3}{10 \times 10^{-6}} \approx 10,000\ h + 18,400\ h = 28,400\ h$$

i.e. more than 3 years.

Furthermore a hydrogen sensor according to the invention was manufactured with a solid electrolyte matrix and tested. The housing was made of polymethylmethacrylate (plexiglass). Activated carbon powder with a specific surface of more than 1,500 m$^2$/g was used for the counterelectrode. The counterelectrode weighed 1.8 g. The solid electrolyte was produced from a mixture of methylacrylate as the monomer, azo-bis(isobutyronitrile) as the initiator and sulphuric acid (38%) by polymerizing at an elevated temperature. The measuring electrode, the separator and the membrane were prepared in the same way as described for the aforementioned sensor. The permissible change in the counterelectrode potential in the solid electrolyte used was 0.6 volts. At a hydrogen concentration of 4% and a polarization voltage of +0.3 volts, the current was 12 $\mu$A. The sensor life was estimated as:

$$t = \frac{400 \times 2.3 \times 0.4}{10 \times 10^{-6} \times 3,600} + \frac{0.08 \times 2.3}{10 \times 10^{-6}} \approx 10,000\ h + 12,000\ h = 22,000\ h$$

i.e. about 2.5 years.

After gassing for 500 hours the sensor was regenerated by reversing the direction of the polarization voltage.

EXAMPLE 2

A sensor according to the invention with measuring, counter and reference electrodes for measuring carbon monoxide concentration was manufactured and tested. The sensor contains a solid electrolyte, a measuring electrode, a counterelectrode and a reference electrode. The solid electrolyte was produced from a mixture of methylmethacrylate as the monomer, azo-bis-(isobutyronitrile) as the initiator and phosphoric acid by polymerisation at an elevated temperature. The measuring electrode and the reference electrode were manufactured from a platinum tube coated with a Teflon membrane. The counterelectrode and the separator were then prepared as described in example 1. The reference electrode is located between the measuring electrode and the counterelectrode and is separated from both by a separator. The permissible change in the counterelectrode potential in the electrolyte used was 0.4 V. The potential of the measuring electrode was kept constant relative to the reference electrode potential by a potentiostatic circuit. For the bias voltage used (potential difference between the measuring and reference electrodes) of 0.1 volts and a CO concentration of 30 ppm in air the sensor current was about 1.5 $\mu$A. The life of the sensor was estimated as follows as in example 1:

$$t = \frac{400 \times 2.3 \times 0.4}{1.5 \times 10^{-6} \times 3{,}600} + \frac{0.08 \times 2.3}{1.5 \times 10^{-6}} \approx 68{,}000 \text{ h} + 120{,}000 \text{ h} = 188{,}000 \text{ h}$$

>20 years

EXAMPLE 3

A hydrogen sensor according to the invention with a supplementary electrode was manufactured and tested. The sensor contains a measuring electrode, a counterelectrode and a solid electrolyte which were manufactured as in example 2. A platinum mesh was used as the supplementary electrode. At the bias voltage used of −0.25 volts between the measuring and counterelectrodes and at a hydrogen concentration of 200 ppm, a cathode (relative to the counterelectrode) current of −550 nA flows in the external conductive circuit. A voltage of +0.15 volts was applied between the supplementary and counterelectrodes which causes an anode (relative to the counterelectrode) current of 500 nA to flow. Thus there is a concurrent charging and simultaneous discharging of the counterelectrode in this sensor. The electrolyte composition does not change so that the life of such a sensor is theoretically unlimited.

EXAMPLE 4

A sensor according to the invention with two measuring electrodes was manufactured and tested. The hydrogen concentration is determined at one of the measuring electrodes and the oxygen concentration at the second measuring electrode. The sensor contains the solid electrolyte described in example 2. A polyethylene foil with a thickness of 20 $\mu$m was used as a diffusion membrane for the hydrogen measuring electrode and of 30 $\mu$m for the oxygen measuring electrode. At the applied voltage of +0.3 volts between the hydrogen measuring electrode and the counterelectrode and a $H_2$ concentration of 400 ppm, a current of 4.5 $\mu$A flows in the external conductive circuit. At a voltage of −0.2 volts between the oxygen measuring electrode and the counterelectrode and an oxygen concentration of about 20.8%, a current of about 5 $\mu$A flows in the external conductive circuit. In this manner charging and discharging of the counterelectrode takes place concurrently. The effective current that causes charging of the counterelectrode is formed from the difference between these two currents and is 5 $\mu$A−4.5 $\mu$A=0.5 $\mu$A since the currents coupled with oxidation of $H_2$ and reduction of $O_2$ have opposite directions. The life of such a sensor is:

$$t = \frac{400 \times 1 \times 0.4}{0.5 \times 10^{-6} \times 3{,}600} + \frac{0.08 \times 1}{0.5 \times 10^{-6}} \approx 89{,}000 \text{ h} + 160{,}000 \text{ h} = 250{,}000 \text{ h}$$

EXAMPLE 5

An electrolyte according to the invention can contain a mixture of acids instead of one acid. A two-electrode sensor according to the invention for determining the carbon monoxide concentration was manufactured and tested. The solid electrolyte was produced from a mixture of methylmethacrylate as the monomer, azo-bis(isobutyronitrile) as the initiator and trifluoro-methanesulfonic acid and phosphoric acid by polymerization at an elevated temperature. Such an electrolyte has a very low hygroscopicity so that it is particularly suitable for sensors with porous diffusion membranes. The permissible change of the counterelectrode potential is 0.2 volts for this electrolyte.

EXAMPLE 6

The electrolyte can be prepared by swelling a polymer containing polymethylmethacrylate in concentrated acid or a mixture of acids.

Two-electrode or three-electrode sensors according to the invention for the determination of gas concentrations were manufactured and tested.

The mixture which is composed of activated carbon powder, polymethylmethacrylate powder and polyethylene powder was heated to 80° C. and pressed under a pressure of 100 kg/cm$^2$. The tablet produced in this way was impregnated with a 85% solution of $H_3PO_4$.

The swelling of methylmethacrylate particles was achieved by heating the tablet at 80° C. for several hours.

Parallel to this polymethylmethacrylate powder was mixed with a 85% solution of $H_3PO_4$ and heated for several hours at 80° C.

The paste prepared in this way was coated on the tablet. The separator and the working electrode were then applied to this and pressed at a pressure of 20 kg/cm$^2$.

EXAMPLE 7

It is also possible to use a solid electrolyte in the separator and for example a liquid electrolyte in the tablet.

A mixture which is composed of activated carbon powder and polyethylene powder was heated at 80° C. and pressed at a pressure of 100 kg/cm$^2$.

The tablet produced in which way was impregnated with a 85% solution of $H_3PO_4$.

Parallel to this polymethylmethacrylate powder was mixed with a 85% solution of $H_3PO_4$ and heated at 80° C. for several hours.

The paste produced in this manner was coated on the tablet. The separator and the working electrode were then applied to this and pressed at a pressure of 20 kg/cm$^2$.

I claim:

1. An electrochemical sensor to determine a gas concentration of a gas to be quantified, comprising a housing, a measuring electrode located within the housing and comprising a catalytically active material which causes a reaction of the gas to be quantified, a counterelectrode located within the housing and comprising a carbon material and a solid electrolyte which is in contact with the measuring electrode and the counterelectrode, wherein the solid electrolyte is prepared by swelling a solid matrix comprising a polymer with an electrolytic solution comprising at least one acid, wherein the polymer is an acrylate polymer or methylacrylate polymer,
   wherein the carbon material in the counterelectrode has a specific surface of at least 40 m$^2$/g and comprises reversibly oxidizable or reducible electrochemically active surface compounds.

2. The electrochemical sensor as claimed in claim 1, wherein the carbon material in the counterelectrode has a specific surface of 1000 to 3000 m$^2$/g.

3. The electrochemical sensor as claimed in claim 1, wherein the catalytically active material in the measuring electrode is selected from the group consisting of platinum, carbon and gold.

4. The electrochemical sensor as claimed in claim 1, wherein the carbon material in the counterelectrode is a porous activated carbon.

5. The electrochemical sensor as claimed in claim 1, wherein the electrochemically active surface compounds comprise hydroquinone and quinone.

6. The electrochemical sensor as claimed in claim 1, wherein the polymer comprises polymethylmethacrylate.

7. The electrochemical sensor as claimed in claim 1, wherein the housing comprises apertures for electrode contacts and a gas chamber having intake apertures and in contact with the measuring electrode.

8. The electrochemical sensor as claimed in claim 7, further comprising a gas-permeable diffusion membrane located between the gas chamber and the measuring electrode.

9. The electrochemical sensor as claimed in claim 1, further comprising a separator which is permeable to ions, located between the measuring electrode and the counterelectrode.

10. The electrochemical sensor as claimed in claim 1, wherein the gas to be quantified is ionized at the measuring electrode to form ions, and the electrolyte contains the ions which are generated in the reduction or oxidation of gas molecules at the measuring electrode.

11. The electrochemical sensor as claimed in claim 1, further comprising a reference electrode.

12. The electrochemical sensor as claimed in claim 1, further comprising a supplementary electrode.

13. The electrochemical sensor as claimed in claim 1, wherein the sensor comprises a plurality of measuring electrodes.

14. A method for quantifying at least one gas, comprising:
providing an electrochemical sensor comprising a housing, a measuring electrode located within the housing and comprising a catalytically active material which causes a reaction of the gas to be quantified, a counterelectrode located within the housing and comprising a carbon material and a solid electrolyte which is in contact with the measuring electrode and the counterelectrode, wherein the solid electrolyte is prepared by swelling a solid matrix comprising an acrylate polymer or methylacrylate polymer with an electrolytic solution comprising at least one acid, wherein the carbon material in the counterelectrode has a specific surface of at least 40 $m^2/g$ and comprises reversibly oxidizable or reducible electrochemically active surface compounds;

setting an external voltage across the measuring electrode and the counterelectrode;

exposing the electrochemical sensor to the at least one gas to be quantified to produce a current; and measuring the current flowing between the measuring electrode and the counterelectrode to quantify the at least one gas to be quantified.

15. The method as claimed in claim 14, wherein the at least one gas to be quantified is at least one member selected from the group consisting of hydrogen, oxygen, carbon monoxide and silane.

16. The method as claimed in claim 14, wherein the at least one gas to be quantified is hydrogen, the measuring electrode comprises platinum, the counterelectrode comprises activated carbon with a specific surface of 1000 to 1700 $m^2/g$, the electrolytic solution comprises a strong mineral acid, and the external voltage is about 0.3 volt.

17. The method as claimed in claim 14, further comprising regenerating the sensor, after said measuring step, by reversing the external voltage set across the measuring electrode and the counterelectrode.

18. A solid electrolyte for use in an electrochemical sensor, comprising the reaction product of a polymer swelled with an electrolytic solution comprising at least one acid, wherein the polymer is an acrylate polymer or methacrylate polymer, wherein the electrolyte is prepared by swelling the polymer in the electrolytic solution, wherein the at least one acid is at least one member selected from the group consisting of sulfuric acid, trifluoromethane-sulfonic acid and phosphoric acid.

* * * * *